United States Patent [19]

David et al.

[11] Patent Number: 4,575,492
[45] Date of Patent: Mar. 11, 1986

[54] PROCESS AND DEVICE FOR THE DETECTION AND QUANTIFICATION OF AGGLUTINATES

[75] Inventors: Pierre David, Verrieres Le Buisson; Jean A. Jarricot, Noisy-Le-Roi, both of France

[73] Assignees: Le Materiel Biomedical; Commissariat a l'Energie Atomique, both of Paris, France

[21] Appl. No.: 602,509

[22] Filed: Apr. 20, 1984

[30] Foreign Application Priority Data

May 2, 1983 [FR] France ............................ 83 07266

[51] Int. Cl.⁴ .................. G01N 21/59; G01N 21/82; G01N 33/53
[52] U.S. Cl. .................................... 436/164; 356/39; 356/442; 422/73; 436/518; 436/805
[58] Field of Search ................ 422/73; 436/805, 164, 436/518, 34; 356/39, 427, 434, 436, 440, 442, 444; 73/64.1

[56] References Cited

U.S. PATENT DOCUMENTS 4,197,088  4/1980  Meserol et al. ............... 422/73 X
4,452,759  6/1984  Takekawa ...................... 422/73

FOREIGN PATENT DOCUMENTS 0046430  2/1982  European Pat. Off. .

*Primary Examiner*—Arnold Turk
*Attorney, Agent, or Firm*—Fisher, Christen & Sabol

[57] ABSTRACT

The present invention relates to a process and device for the detection and quantification of agglutinates, in recipients of which at least the bottom are transparent. According to the invention, it is decided that there is agglutination when, at the same time, the calculated mean value of the bottom of the reaction studied is higher than that of a reference sample and when there exist points of measurement whose transmission is less than said threshold, and, on the other hand, that there is no agglutination when, at the same time, this calculated mean value is not greater than that of said reference sample and when there exist no points of measurement whose transmission is less than said threshold. The invention is more particularly applicable to immunohaematology.

6 Claims, 7 Drawing Figures

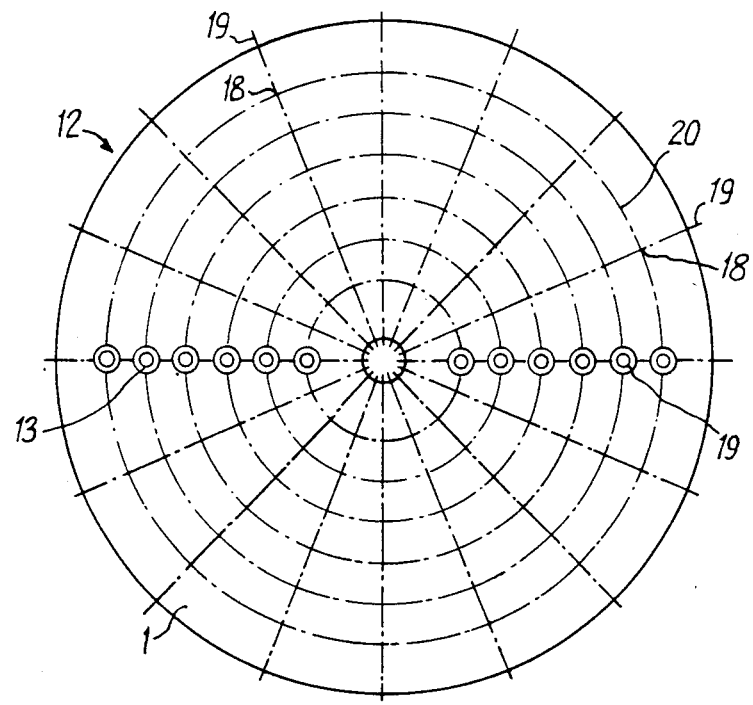
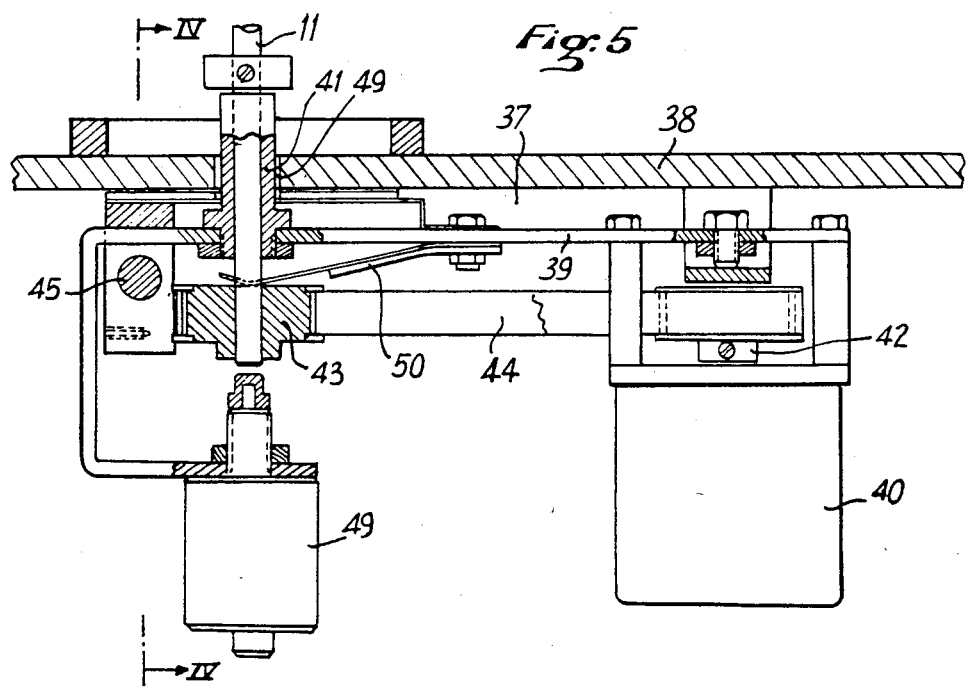

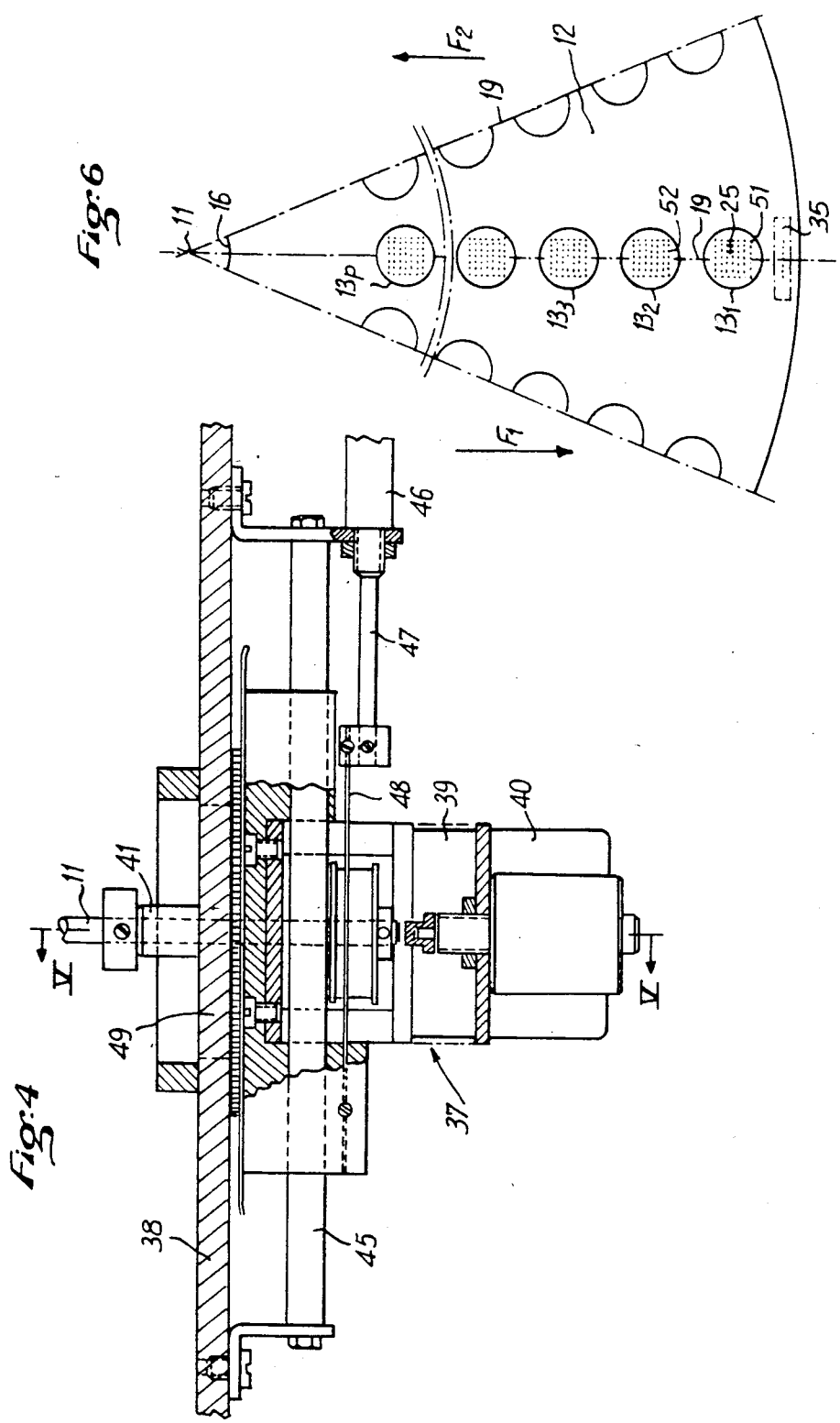

PROCESS AND DEVICE FOR THE DETECTION AND QUANTIFICATION OF AGGLUTINATES

The present invention relates to a process and a device for the detection and quantification of agglutinates capable of being formed, under the action of at least one reagent, by particles in suspension in a liquid.

It may be used whenever agglutinates are to be detected and quantified. However, it is particularly applicable in immunohaematology, particularly with a view to determining blood groups. In fact, the determination of blood groups is known to be associated with the search for the existence in the blood of erythrocyte antigens. The immunocytological reactions, faced with an antigen of specific group, are translated by a phenomenon of agglutination of the red blood corpuscles, (particularly if the latter belong to another group). These red blood corpuscles may form either uniform agglutinates without free red blood corpuscles, or some large agglutinates, or again a large number of small agglutinates.

Although the present invention is not limited in its applications to immunohaematology, it will be described hereinafter more especially in connection with this particular application.

Devices for the detection and quantification, in recipients of which at least the bottoms are transparent, of agglutinates capable of being formed under the action of at least one liquid reagent, by particles in suspension in doses of liquids to be tested contained in said recipients, are already known, such devices comprising a linear arrangement of a plurality n of photosensitive elements observing by transparency the bottoms of said recipients containing the possible agglutinates by scanning said bottoms of said recipients, so as to form $n \times m$ points of observation distributed over a rectangular or square surface occupying the major part of the surface of the bottom of each recipient.

In these known devices, for each point of observation, the transmission of light measured is compared with a predetermined light transmission threshold and, for this point of observation, it is decided that there is agglutination if the transmission of light measured is less than said threshold and that there is no agglutination if this transmission of light measured is greater than said threshold. Such a threshold may be fixed and determined as a function of prior measurements. However, such a threshold risks not being exactly adapted to the measurements underway, and not enabling low levels of agglutination to be measured and detected. A positive reaction will then be considered as negative for the device.

To avoid this drawback, it has already been envisaged to determine the threshold from the mean value of the transmission of a reference sample not comprising agglutinates. However, in order to overcome variations in transmission between reference sample and samples being measured, due to differences either of concentration or of sizes of the particles, it is in fact necessary, in that case, to determine two thresholds surrounding this mean value. The errors of qualification and of interpretation which would be due to such differences are thus eliminated, since it is then considered that the values of transmission included in the band between the two thresholds correspond to free, non-agglutinated particles, whilst the values of transmission lower and higher than said band correspond respectively to an agglutination and to the (empty) background of the image. However, although it allows certain errors to be avoided, this method introduces others, since, due to the width of the band between the two thresholds, there is a risk, in a measurement, of considering as non-agglutinated particles which, in fact, present a slight agglutination. Moreover, a device for carrying out this method is complicated due to the presence of two thresholds.

In addition, whether the threshold is fixed or connected with the mean value of the transmission of a reference sample, the known devices functioning according to this principle are particularly imprecise, since they consider as agglutinates totally foreign phenomena such as artefacts, solid particles (fibrin), dust, micro-clots, etc . . . capable of causing a considerable, if not total, absorption of light.

It is an object of the present invention to overcome these drawbacks. It enables high-precision results to be obtained by taking all the agglutinates, even the weakest ones, into account, whilst employing a particularly simple device for execution thereof.

To this end, according to the invention, the process for the detection and quantification, in recipients of which at least the bottoms are transparent, of reactions of agglutination capable of being produced, under the action of at least one liquid reagent, by particles in suspension in doses of liquids to be tested contained in said recipients, an arrangement of a plurality of photosensitive elements observing by transparency the bottoms of said recipients containing the possible agglutinates, so as to form $n \times m$ points of measurement distributed over a rectangular or square surface occupying the greater part of the surface of the bottom of each recipient, process whereby, for each point of measurement, the transmission of light measured is compared with a light transmission threshold which is connected with the mean value of the transmission of a plurality of points of measurement of a reference sample in which there is no agglutination, with the result that any value of transmission less than this threshold might be considered as representative of an agglutination, is noteworthy in that, for each reaction recipient, the mean value of the transmission of the points of measurement whose transmission is greater than said threshold is measured, this mean value is compared with that of said reference sample and it is considered, on the one hand, that there is agglutination when, at the same time, this mean value of the transmission is higher than that of said reference sample and when there exist points of measurement whose transmission is less than said threshold, and, on the other hand, that there is no agglutination when, at the same time, this mean value is not greater than that of said reference sample and when there exist no points of measurement whose transmission is less than said threshold.

Thus, according to the invention, a positive reaction of agglutination is characterized by the coincidence of a positive variation of the mean value of the transmission and of the presence of points with transmission less than the mean value of the reference sample. Inversely, a negative reaction of agglutination is characterized by the absence of variation of the mean value of the transmission and the absence of points with transmission less than the mean value of transmission of the reference sample. Any other type of reaction is then rejected.

Thanks to the invention, the criteria of classification of the reactions are therefore considerably improved and it is therefore possible to choose an optimally adjusted transmission threshold.

In a preferred embodiment of the process according to the invention, for each recipient, in addition to counting the points of measurement whose transmission is less than said threshold, the points whose transmission is higher than said threshold are counted, the transmissions of the points whose transmission is higher than said threshold are summed, and the mean value of the transmission of the points whose transmission is higher than said threshold is calculated.

In order to determine said threshold, the bottom of a recipient which is identical to the reaction recipients but which contains a reference sample not subject to agglutination may be observed by transparency at a plurality of points of measurement, the points whose transmission is higher than x % are counted, the transmissions of the points whose transmission is higher than x % are summed, and the mean value of the transmission of said points is calculated. It is then advantageous, in order to obtain said threshold, to deduct from the mean value thus obtained, a certain percentage of transmission, determined by experience, and corresponding to parasitic points with weak transmission such as dust, artefacts, grease spots, etc . . . , to the absorption of the bottom of the recipient, to the heterogeneity of the photosensitive elements, etc . . .

However, preferably, in order to determine said threshold, the bottom of a recipient which is identical to the reaction recipients but which contains a reference sample not subject to agglutination is observed by transparency, at a plurality of points of measurement, the transmission of each point of measurement is compared with an arbitrary reference and the number of points of measurement for which the transmission is less than said reference is counted. This number of points counted is compared with a number of points predetermined by experience and corresponding to parasitic points with weak transmission, then if this number of points counted is greater than said predetermined number, the value of said reference is progressively readjusted until the number of points counted is less than said predetermined number of points.

According to another aspect of the invention, a device for the detection and quantification, in recipients of which at least the bottoms are transparent, of agglutinates capable of being formed, under the action of at least one liquid reagent, by particles in suspension in doses of liquids to be tested contained in said recipients, device comprising an arrangement of a plurality of photosensitive elements observing by transparency the bottoms of said recipients containing the possible agglutinates so as to form n×m points of observation distributed over a rectangular or square surface occupying the greater part of the surface of the bottom of each recipient, is noteworthy in that it comprises, in combination:

comparison means of which one input is connected to said photosensitive elements, of which the other input receives a signal representative of a light transmission threshold and of which the output is connected to counting means counting the points of measurement of which the transparency is less than said threshold;

peak value detection means connected to said photosensitive elements;

summation means receiving the output signal from said peak value detection means and summing the peak values of the signals emitted by said photosensitive elements when the response of the latter corresponds to a transmission greater than said threshold;

means for memorizing the sum furnished by said summation means;

means for counting the points of measurements whose transparency is greater than said threshold; and a microprocessor connected to said counting means and to said memorizing means in order to calculate, for each recipient, the mean value of the sum recorded in said memorizing means, to compare this calculated mean value with the corresponding mean value of a reference sample and to decide that there is agglutination when, at the same time, this calculated mean value is higher than that of said reference sample and when there exist points of measurement whose transparency is less than said threshold and, on the other hand, that there is no agglutination when, at the same time, this calculated mean value is not greater than that of said reference sample and when there exist no points of measurement whose transmission is less than said threshold.

The arrangement of photosensitive elements may be of the charge coupled diode bar type, generally designated by the letters CCD, DTC or CCPD. According to the invention, in which a rectilinear bar of n charge coupled devices is used, observation is effected, with a view to detecting the possible agglutinates and during the relative movement of each transparent bottom of the recipient at m positions spaced apart and parallel to said bar, so as to form n×m points of observation distributed over a rectangular or square surface occupying the major part of the surface of said bottom. Of course, n may be chosen to be equal to m and the distance between two consecutive positions of observation of the bar may be arranged to be equal to the distance between two CCD devices of the bar. In this way, a square surface of the transparent bottom is totally covered. For example, the rectilinear bar comprises 256 CCD photodiodes, each having a definition of 25 $\mu$m, the video data being digitized at 256 levels of grey, and the analyzed image represents a square centred on said transparent bottom and formed by 256 scannings spaced apart by 25 $\mu$m.

For observing the agglutinates and for each recipient, n×m measurements are thus obtained, distributed in m scannings of n points.

The invention will be more readily understood on reading the following description with reference to the accompanying drawings, in which:

FIG. 3 is a plan view of a recessed disc used in the device according to the invention.

FIGS. 4 and 5 are sections along lines IV—IV and V—V respectively of FIG. 2.

FIG. 6 schematically illustrates the process of reading the agglutinates.

Figure 7:
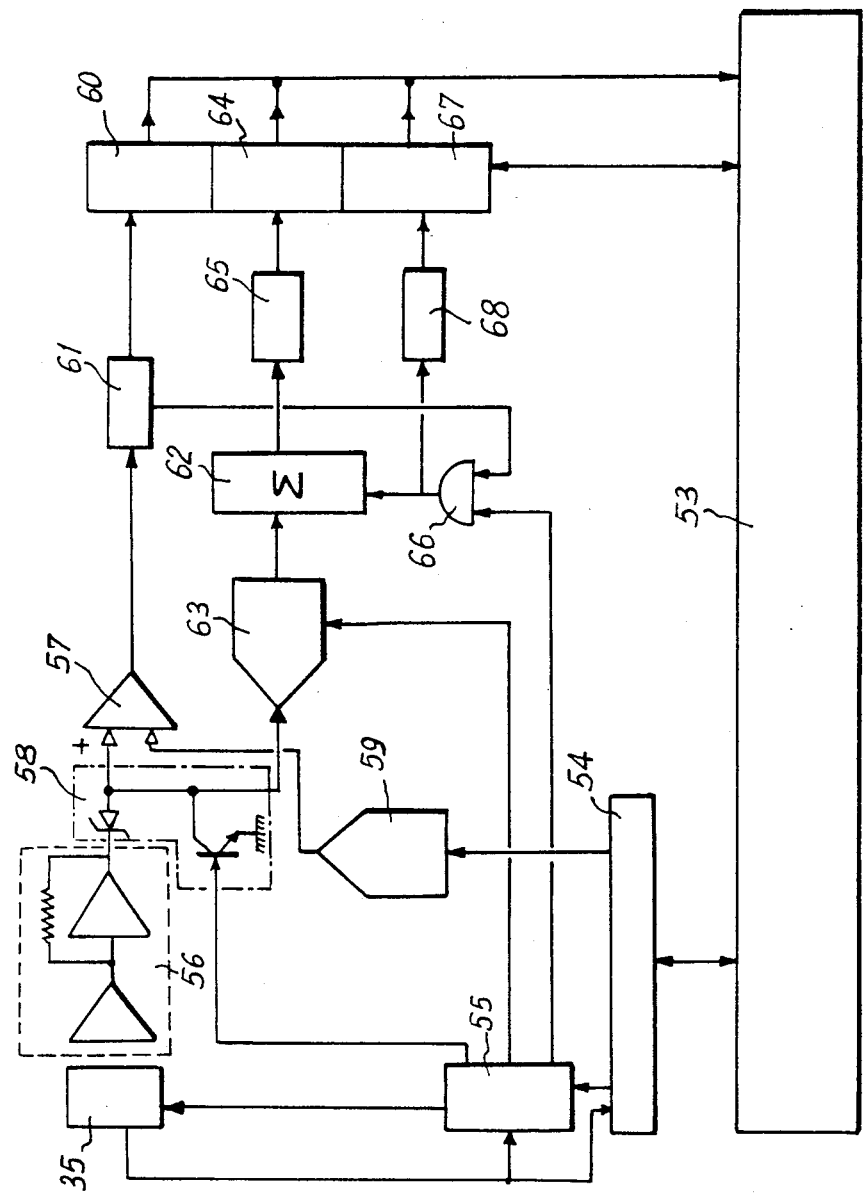

FIG. 7 gives the block diagram of the reading and quantification device of the device according to the invention.

In these Figures, like references designate like elements.

Figure 1:
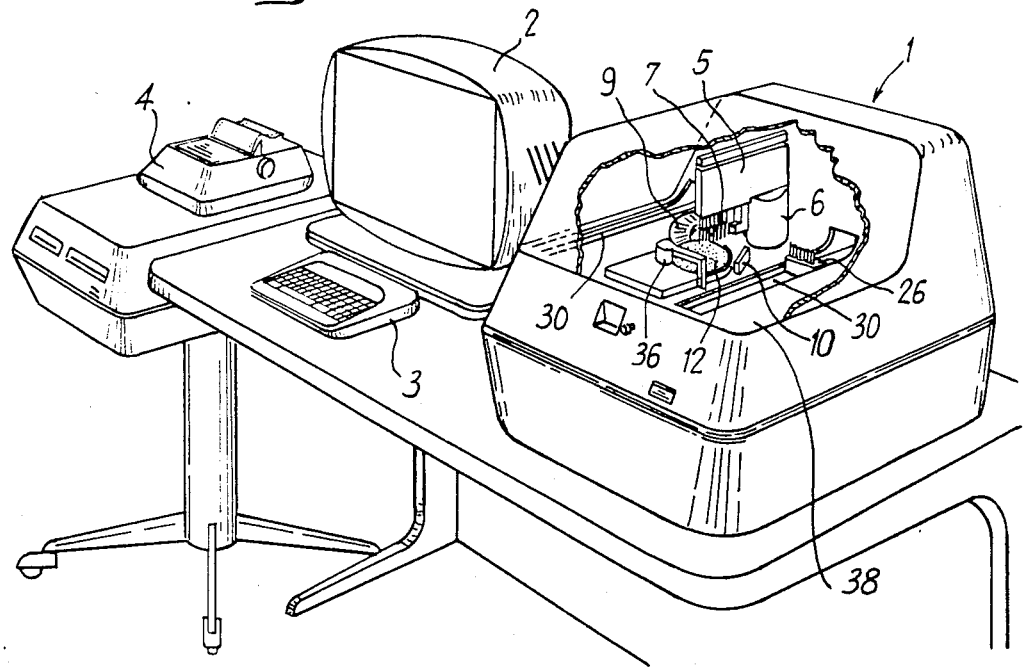
FIG. 1 is an overall view in perspective, with parts torn away, of an installation with the device according to the invention.

Referring now to the drawings, the installation for recognizing blood groups, shown in FIG. 1, comprises a device 1 according to the invention for the detection and quantification of agglutinates, associated with a display device 2, with a control device 3 and with a printout device 4. The whole of the installation is controlled by a microprocessor 53 (cf. FIG. 7).

Figure 2:
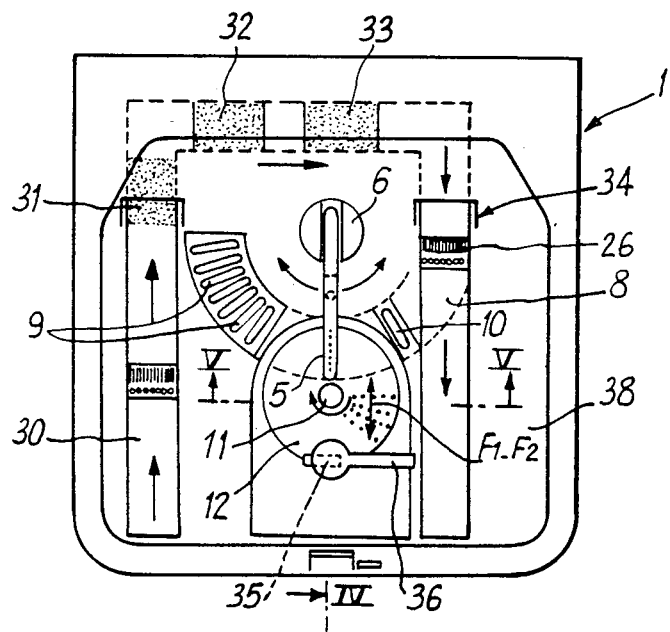
FIG. 2 is a simplified plan view of the device according to the invention.

As may also be seen in FIG. 2, the device 1 according to the invention comprises a horizontal oscillating arm 5 adapted to rotate about a vertical shaft 6 and to slide therealong. The arm 5 bears a plurality of vertical syringes 7, of which the pistons may be actuated to draw in or deliver a liquid. When the arm 5 oscillates about the vertical shaft 6, the syringes 7 sweep over an annular zone 8.

In this annular zone 8 are provided recipients 9 with reagents in each of which the vertical syringes 7 may draw off a reagent, and a recipient 10 for rinsing.

Furthermore, the device 1 comprises a vertical shaft 11 adapted to rotate a disc 12 of transparent material in which recesses 13 are made. As shown in FIG. 3, the disc 12 is made of transparent synthetic material and is provided at its centre with a hole 16 to allow passage of the rotary drive shaft 11.

The recesses 13 are distributed at a plurality of points 18 lying at the intersection of radii 19 and of concentric circles 20. Only a few recesses 13 have been shown in FIG. 3 in order to render the drawing clearer.

The annular zone 8 over which the syringes 7 sweep intersects the disc 12 with the result that it is possible to fill all the recesses 13 disposed on a radius 19 of the disc 12, with doses of reagents coming from the containers 9 by introducing the needles of the syringes 7 into said recesses 13. In the same way, it is possible to introduce into the recesses 13 doses of liquids coming from reserves 26 located in zone 8.

The containers 26 are introduced into the device 1 by a conveyor 30 which passes them successively to different treatment stations 31, 32 and 33, before taking them to station 34 where the syringes 7 of the arm 5 can take the liquid that they contain.

In this way, each recess 13 of the disc 12 may serve as recipient for reaction between a liquid coming from a container 26 and a reagent coming from a recipient 9.

In order to examine the result of agglutination which may result therefrom, the device 1 comprises a bar 35 of CCD diodes disposed under the disc 12 opposite a lighting device 36. The bar 35 and the lighting device 36 are opposite the arm 5 with respect to the shaft 11 and the bar 35 is at right angles to the vertical plane defined by axes 6 and 11.

The bar 35 examines by transparency the bottom 25 of each recess 13 in m observations each offset by one step. For all the recesses 13 of a radius 19 of the disc 12 to be able each to be examined in m steps, the shaft 11 of said disc is rendered mobile in horizontal translation, at right angles to said bar 35 (arrows $F_1$ and $F_2$ of FIG. 2 and FIG. 6).

To that end, FIGS. 4 and 5 show that the shaft 11 of the disc 12 is fast with a carriage 37 mobile with respect to the base plate 38 of the device. This carriage 37 comprises a frame bearing a motor 40 and a smooth bearing 41 for the shaft 11. The driven shaft of the motor 40 rotates a pulley 42 which is connected to a pulley 43 fitted on the shaft 11, via a notched belt 44. The carriage 37 is guided in translation by a rail 45 and it moves under the action of a jack 46, whose rod 47 is connected to the carriage 37 by a rod 48.

In this way, the shaft 11 may slide in a slot 49 in the base plate 38 parallel to the rail 45 and at right angles to the bar 35 of CCD diodes.

The carriage 37 may moreover bear a vibrator 49 adapted episodically to animate the shaft 11, against the action of a spring 50, in a reciprocating movement parallel to its axis, in order possibly to stir the liquid contained in the recesses 13 in the disc 12.

When the recesses $13_l$ to $13_p$ of the radius 19 lying in the plane defined by axes 6 and 11 are to be read by the arrangement 35 in order to detect and quantify the agglutinations (cf. FIG. 6), the disc 12 is advanced by the jack 46 in the direction of arrow $F_1$ for the arrangement 35 to be plumb with the outer limit 51 of the field 25 of the bottom of the first recess $13_1$. Then, step by step, the jack is displaced m times for the n photosensitive elements of the arrangement 35 to examine said field 25 at $n \times m$ points. When reading of the field 25 of the recess $13_1$ is terminated, the jack 46 displaces shaft 11, still in the same direction $F_1$, so that the outer limit 52 of the field 25 of the bottom of the second recess $13_2$ arrives plumb with the photosensitive elements of arrangement 35. This second recess $13_2$ is read in identical manner and the process continues until recess $13_p$ has been completely read. After the latter, the jack 46 returns shaft 11 into its initial position (arrow $F_2$).

FIG. 7 illustrates the device for reading and qualification of the agglutinates by means of a microprocessor 53. The latter may also pilot the whole of the automatic control of the installation according to the invention (movements of arm 5; actuation of syringes 7, . . . ) in accordance with a process which will not be described hereinafter.

Via an input-output device 54 and a sequencer 55, the microprocessor 53 controls the device of FIG. 7. The latter comprises the network 35 of CCD diodes, of which the output signal is amplified by a video amplifier 56. At the output of the amplifier 56 are disposed a comparator 57 with two inputs and a peak value detector 58. One of the inputs of the comparator 57 receives the amplified video signal leaving the amplifier 56, whilst the other input of said comparator receives a threshold furnished by the microprocessor 53, via a digital-to-analog converter 59.

The output of the comparator 57 is connected to an upcounter (or downcounter) 60, via a shaping device 61.

Furthermore, the output of the peak value detector 58 is connected to a summation device 62, via an analog-to-digital converter 63. The output of said summation device 62 is connected to an upcounter (or downcounter) 64, via a shaping device 65.

The summation device 62 comprises a control input capable of inhibiting operation of said summation device, and controlled by the output of a gate 66 which receives at its inputs a signal coming from the sequencer 55 and of which each impulsion corresponds to a point of measurement and a signal from the shaping device 61. Moreover, the output of the gate 66 is connected to an upcounter (or downcounter) 67, via a shaping device 68.

Counters 60, 64 and 67, which may form one sole counting unit, are controlled by the microprocessor 53 which, furthermore, receives the contents thereof.

In order to be able subsequently to detect and quantify agglutinates corresponding to reactions taking place in recesses 13, a sample liquid dose (reference), of the same nature as the liquid doses capable of agglutination under the effect of the reagents, but in which it is certain that no agglutination takes place, is firstly studied.

To this end, the recess 13 containing the dose of the reference sample is brought opposite the light source 36 and the bar of diodes 35 and the process of scanning of said reference sample at n×m points is set into motion.

For example, the microprocessor 53, which also co-ordinates said scanning, imposes on the comparator 57, via the converter 59, a threshold S corresponding to a light transmission equal to x %, x being for example equal to 50. The transmission of each of the n×m points of measurement of the reference sample is compared with this threshold S and the comparator 57 trips, i.e. emits a signal, whenever the transmission of a point of measurement is less than said threshold S, i.e. whenever this point of measurement has an opacity greater than x %. The counter 60 therefore counts the number of these points more opaque than x %. Moreover, the summation device 62 sums the value of the opacities of the points of measurement, except when it is prevented from doing so by the action of the shaping device 61, which occurs whenever a point of measurement has an opacity greater than x %.

Consequently, the counter 64 records the sum of the opacities of the points having an opacity less than x %. The output of the gate 66 validates the summation of the summation device 62 only if the comparator 57 has not tripped, i.e. if the output of the gate 66 is representative of the number of points of which the opacity is less than x %. The counter 67 therefore records the number of said points with opacity less than x %. From the contents of counters 64 and 67, the microprocessor 53 easily deduces the mean value Vm of the transmission of the n×m points of measurement of the reference sample. The microprocessor 53 may use this mean value Vm as threshold. However, in order to take into account parasitic responses due to physical or biological effects (heterogeneity of the diodes 35, transmission of the bottom of the recesses, dust, artefacts, etc . . . ), it is preferable if the microprocessor adopts as threshold Sx the mean value Vm corrected by subtraction of a certain percentage of transmission, corresponding to these effects and determined by experience.

According to a finer variant of the process of calculation of such a threshold Sx, the microprocessor 53 may employ an iterative method. For example, as before, an arbitrary threshold of x % is applied to the comparator 57 and the number of trips of the comparator 57 is counted. This number of trips is transmitted to the microprocessor 53 which automatically readjusts the value of the threshold until the number of trips counted is as close as possible to the predetermined percentage of the total number of the points of measurement read, this percentage, as before, being determined by experience and corresponding to the parasitic responses.

Whatever the mode of determination of the threshold Sx, the latter is then used for measurements on liquid doses subjected to reagents. To this end, the different recesses 13 containing a liquid dose of the same type as the sample are examined and the microprocessor 53 applies on the corresponding input of the comparator 57 the corresponding threshold Sx. Thus, for each of the n×m points of observation of a recess, in the manner indicated hereinabove, counter 60 stores the number of points corresponding to agglutinates, counter 64 stores the sum of the intensities of the points not corresponding to agglutinates and counter 67 stores the number of points not corresponding to agglutinates.

From the measurements stored in the three counters 60, 64 and 67, the microprocesor 53 calculates the mean value of transmission of the non-agglutinated points (by division of the contents of counters 64 and 67). It compares this mean value of transmission with that of the reference sample and in the event of it establishing, simultaneously, that the result of this comparison shows that this mean value is greater than that of the points of the reference sample and that counter 60 contains agglutinated points, it decides that there is indeed agglutination.

Of course, as a function of the intensity of this agglutination, it may classify the latter in the different classes usual in microbiology.

Moreover, when the microprocessor 53 simultaneously establishes that the mean value of transmission calculated is not greater than that of the reference sample and that counter 60 does not contain agglutinated points, it decides that there is no agglutination.

What is claimed is:

1. Process for the detection and quantification, in recipients of which at least the bottoms are transparent, of reactions of agglutinations capable of being produced, under the action of at least one liquid reagent, by particles in suspension in doses of liquids to be tested contained in said recipients, comprising: observing by transparency the bottoms of said recipients containing the possible aggluintates, at n×m points of measurement distributed over a rectangular or square surface occupying the greater part of the surface of the bottom of each recipient; measuring the light transmission of a plurality of points of a reference sample in which no agglutination has taken place; determining a light transmission threshold which is connected with the mean value of transmission of said plurality of points of measurement of said reference sample; measuring the light transmission of a plurality of points of a test liquid; calculating the mean value of the transmission of the points of measurement whose transmission is greater than said threshold; comparing this mean value with that of said reference sample; and determining, on the one hand, that there is agglutination when, at the same time, this mean value of the transmission is higher than that of said reference sample and when there exists points of measurement whose transmission is less than said threshold, and, on the other hand, that there is no agglutination when, at the same time, this mean value is not greater than that of said reference sample and when there exists no points of measurement whose transmission is less than said threshold.

2. The process of claim 1, wherein, in order to determine said threshold, the bottom of a recipient which is identical to the reaction recipients but which contains a reference sample not subject to agglutination is observed by transparency, at a plurality of points of meausrement, the transmission of each point of measurement is compared with an arbitrary reference and the number of points of meaurement for which the transmission is less than said reference is counted, this number of points counted is compared with a predetermined number of ordinarily-encountered parasitic points having weak transmission, then if this number of points counted is greater than said predetermined number, the value of said reference is progressively readjusted until the number of points counted is less than said predetermined number of points.

3. The process of claim 1, wherein the points of measurement whose transmission is less than said threshold are counted.

4. The process of claim 1, wherein, in order to determine said threshold, the bottom of a recipient which is identical to the reaction recipients but which contains a reference sample not subject to agglutination is observed by transparency at a plurality of points of measurement, the points whose transmission is higher than 50 percent are counted, the transmissions of the points whose transmission is higher than 50 percent are summed, and the mean value of the transmission of said points is calculated.

5. The process of claim 4, wherein, in order to obtain said threshold, a certain predetermined percentage of transmission, which takes into account normally encountered parasitic points having weak transmission, is deducted from the mean value thus obtained.

6. Device for the detection and quantification, in recipients of which at least the bottoms are transparent, of agglutinates capable of being formed, under the action of at least one liquid reagent, by particles in suspension in doses of liquids to be tested contained in said recipients, said device comprising:

(a) an arrangement of a plurality of photosensitive elements observing by transparency the bottoms of said recipients containing the possible agglutinates so as to form n×m points of observation distributed over a rectangular or square surface occupying the greater part of the surface of the bottom of each recipient;

(b) comparison means of which one input is connected to said photosensitive elements, of which the other input receives a signal representative of a light transmission threshold and of which the output is connected to counting means counting the points of measurement of which the transparency is less than said threshold;

(c) peak value detection means connected to said photosensitive elements;

(d) summation means receiving the output signal from said peak value detection means and summing the peak values of the signals emitted by said photosensitive elements when the response of the latter corresponds to a transmission greater than said threshold;

(e) means for memorizing the sum furnished by said summation means;

(f) means for counting the points of measurements whose transparency is greater than said threshold; and (g) a microprocessor connected to said counting means and to said memorizing means in order to calculate, for each recipient, the mean value of the sum recorded in said memorizing means, to compare this calculated mean value with the corresponding mean value of a reference sample and to determine that there is agglutination when, at the same time, this calculated mean value is higher than that of said reference sample and when there exists points of measurement whose transparency is less than said threshold and, on the other hand, that there is no agglutination when, at the same time, this calculated mean value is not greater than that of said reference sample and when there exists no points of measurement whose transmission is less than said threshold.

* * * * *